United States Patent [19]

Nishimura et al.

[11] Patent Number: 4,789,929
[45] Date of Patent: Dec. 6, 1988

[54] CT SYSTEM FOR SPIRALLY SCANNING SUBJECT ON A MOVABLE BED SYNCHRONIZED TO X-RAY TUBE REVOLUTION

[75] Inventors: Hiroshi Nishimura; Osamu Miyazaki, both of Chiba, Japan

[73] Assignee: Hitachi Medical Corporation, Japan

[21] Appl. No.: 49,802

[22] Filed: May 14, 1987

[51] Int. Cl.[4] .......................... A61B 6/03; G01N 23/04
[52] U.S. Cl. ................................ 364/413.15; 378/20; 364/413.21
[58] Field of Search ........................... 364/414; 378/20

[56] References Cited

U.S. PATENT DOCUMENTS 4,433,380 2/1984 Abele et al. ..................... 364/414

FOREIGN PATENT DOCUMENTS 0170746 9/1985 Japan .

Primary Examiner—Jerry Smith
Assistant Examiner—Clark A. Jablon
Attorney, Agent, or Firm—Gerald J. Ferguson, Jr.

[57] ABSTRACT

A computerized tomography system which includes an X-ray generator for producing X-rays, an X-ray detector array for detecting the X-rays transmitted through a subject, and a subject bed. The X-ray tube and the X-ray detectors are opposed to each other, and the X-ray beams are irradiated upon the subject in a sectorial manner at a large number of angles to scan the subject while the X-ray tube and the X-ray detectors are being revolved around the subject, the X-ray tube and X-ray detectors remaining opposed to each other the during revolution. The system includes a system for rapidly and continuously revolving a frame bearing the X-ray tube, a system for moving the subject bed perpendicularly to a plane of revolution of the X-ray tube and for moving the subject bed synchronously with the revolution of the X-ray tube, a system for scanning the subject along with the movement of the subject bed in a spiral with respect to a coordinate system positioned about an imaginary axis passing through the subject, and a system for obtaining a reconstructed tomogram of an arbitrary cross-section within a range from a position corresponding to a beginning of the spiral scanning to a position corresponding to an end of the spiral scanning. A method of operating the computerized tomography system is also provided.

20 Claims, 10 Drawing Sheets

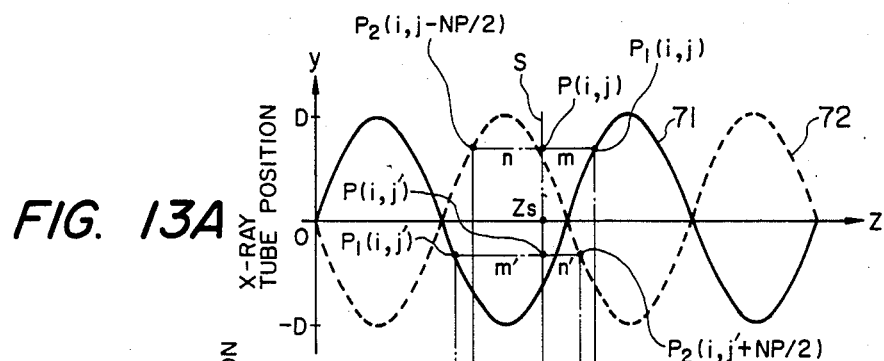
FIG. 13A
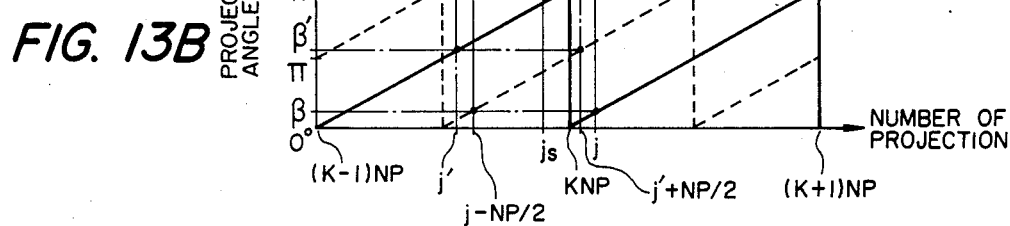
FIG. 13B
FIG. 15
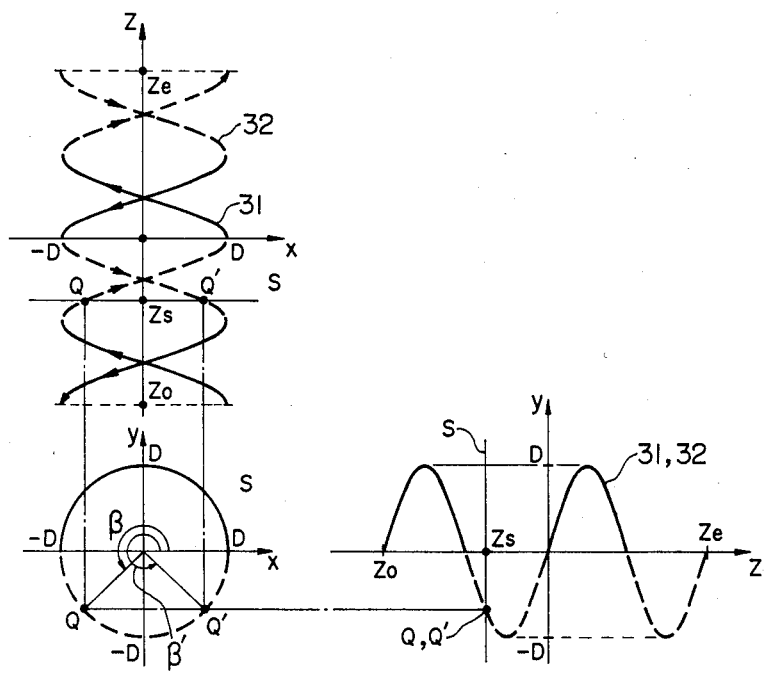

CT SYSTEM FOR SPIRALLY SCANNING SUBJECT ON A MOVABLE BED SYNCHRONIZED TO X-RAY TUBE REVOLUTION

BACKGROUND OF THE INVENTION

The present invention relates to a computerized tomographic system in which a frame bearing an X-ray tube can be continuously rotated.

The computerized tomography machine is now an indispensable diagnostic machine in radiology. To photograph the mutually-continuous slices of a subject (patient) by a conventional third-generation computerized tomographic system, X-rays are irradiated upon the slices, without moving the subject bed, until the end of each scanning period. The subject bed is moved at the end of each scanning period to take the photograph of the next slice. For that reason, the downtime between the scanning of each slice cannot be eliminated. Therefore, it takes long time to take all the necessary photographs by the conventional tomographic system, presenting problems for the users of the system.

If the photography time is shortened, the period of restraint on the subject is reduced, which results in increasing the number of photographed subjects. Therefore, it is economically important to shorten the photographing time.

SUMMARY OF THE INVENTION

The present invention was made in consideration of the above-mentioned problem.

Accordingly, it is an object of the present invention to provide a third-generation or fourth-generation computerized tomographic system whose computerized tomographic scan photographing time is reduced to shorten the period of restraint on each subject to increase the number of photographed subjects.

The computerized tomography machine provided in accordance with the present invention comprises a high voltage supply unit made of a slip ring or the like and means for collecting and transmitting X-ray measurement data. The tomography machine can be continuously rotated. In other words, the tomography machine can be rotated more than an angle range of 360°. The angle range of the rotation of the tomography machine is not limited by the length of a cable or the like.

Because all photographed data is stored once in a buffer means, the capacity of the buffer means must be large. However, one of the two two-dimensional buffers is used for data collection and the other is used for DMA (direct memory access) transfer to a disk, so that the existing technology can deal well with the storage of all the photographed data. If the costs of memories are lowered further in the future, it will be easier to embody the present invention.

It is easy to obtain a reconstructed three-dimensional tomogram from computerized tomographic scans made from the data obtained by using the computerized tomography machine according to the present invention.

Since it is presumable that artifacts are caused by the lack of constant speed of the subject bed, it is necessary to move the subject bed at a constant speed to properly exercise the present invention.

According to the present invention, the subject is irradiated with X-rays to scan the particular portion thereof while an X-ray tube and X-ray detectors opposed thereto are revolved around the subject. At the same time, the subject bed is moved perpendicularly to the plane of the scanning and synchronously with the scanning, to rapidly and continuously perform the scanning to reconstruct the three-dimensional tomogram. The subject can thus be rapidly and continuously scanned throughout the movement of the subject bed.

According to the present invention, the downtime which would conventionally be caused in cardiac scanning for photographing a heart through continuous revolution as the subject bed remains stationary can be decreased. The downtime which would conventionally be caused in the dynamic scanning of the liver, brain or the like to photograph it through continuous revolution as the subject bed remains stationary can also be decreased.

BRIEF DESCRIPTION OF THE DRAWINGS

The invention will now be described in greater detail with reference to an embodiment of the present invention given solely by way of example and illustrated in the accompanying drawings, in which:

FIGS. 13A and 13B show the downward projection of the locus of the X-ray tube toward the subject and the relationship between the angle of the projection and the number of each projection in the forward and the backward scannings;

FIG. 15 shows the downward projection of the locus of an X-ray tube toward a subject and the relationship between the angle of the projection and the number of each projection in forward and backward scannings;

DETAILED DESCRIPTION OF PREFERRED EMBODIMENTS

Embodiments of the present invention are hereafter described with reference to the drawings attached hereto.

Figure 1:
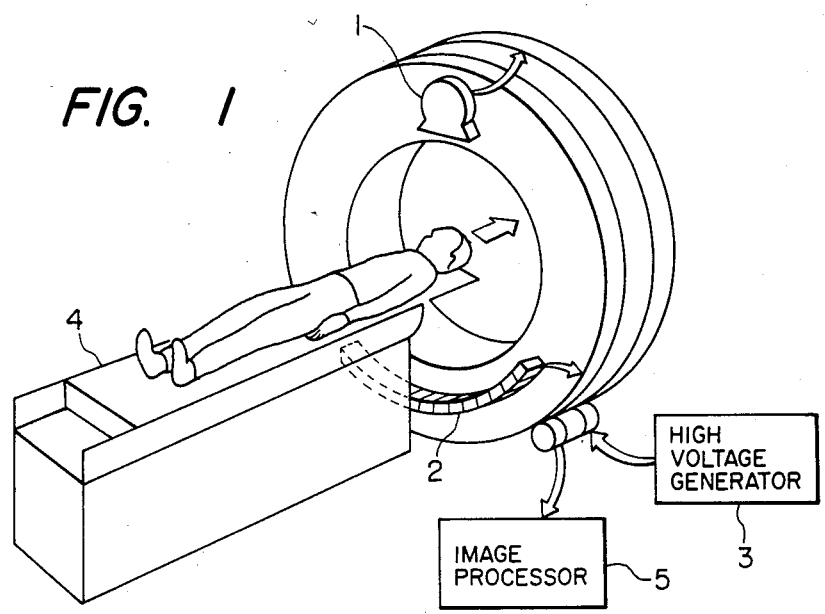
FIG. 1 shows a view for describing the outline of the present invention.

FIG. 1 shows the outline of the first embodiment which is a third-generation computerized tomography machine of the rotate-rotate type for medical care. The tomography machine includes X-ray tube 1, X-ray detectors 2, high voltage generator 3, subject bed 4 and image processor 5. A high voltage is applied to X-ray tube 1 by a power supply means (not shown) made of a slip ring or the like. Measured data obtained through the array of X-ray detectors 2 are converted into digital signals by a large number of A/D converters. The digital signals are received through a photocoupler or the like from a frame (scanner) bearing the X-ray tube. The scanner is capable of continuous scanning by rapid continuous rotation. Subject bed 4 can be moved at a constant speed either backward or forward perpendicularly to the plane of rotation of the scanner.

The irradiation of X-rays, the movement of the subject bed and the revolution of the X-ray tube can be synchronized with each other by either a mechanical method or an encoding method. In the mechanical method, a rotary motion from a drive system for rotating the frame is transmitted through a gear system to rotate a feed screw to easily move the subject bed perpendicularly to the plane of rotation of the scanner. The speed of the rotation of the scanner and that of the movement of the subject bed are completely related to each other to synchronize rotation and movement with each other. In the encoding system, an encoder, which is attached to a rotary plate and provided so that black and white patterns replace each other at each prescribed angle, is disposed for an angle of 360°, and a photosensor is secured to a stationary gantry. The rotary encoder moves across the photosensor so that the angular velocity of the rotation of the encoder is detected. The detected angular velocity is applied to a DC servomotor or the like for moving the subject bed, and to synchronize the irradiation of the X-rays, the movement of the subject bed and the revolution of the X-ray tube with one another. The encoding system is adopted in this embodiment.

It is obvious that the present invention can be also applied to the situation in which the scanner is the same as that of a fourth-generation computerized tomography system of the stationary-rotate type in which a large number of X-ray detectors are placed along an angle range of 360° and only the X-ray tube is rotated.

As for a conventional computerized tomography machine, the subject bed is moved according to each unitary slice thickness, such as 2 mm, 3 mm, 5 mm and 10 mm, at the end of photographing of each slice plane (usually based on a revolution throughout the angle range of 360°) and not moved during the photographing. For that reason, the scanner of the tomography machine needs to be rotated through an angle range of 360° and cannot be rotated continuously.

The present invention is characterized by providing a mechanism which makes it possible for the scanner to be continuously rotated and the subject bed to be moved at a constant speed.

Figure 2:
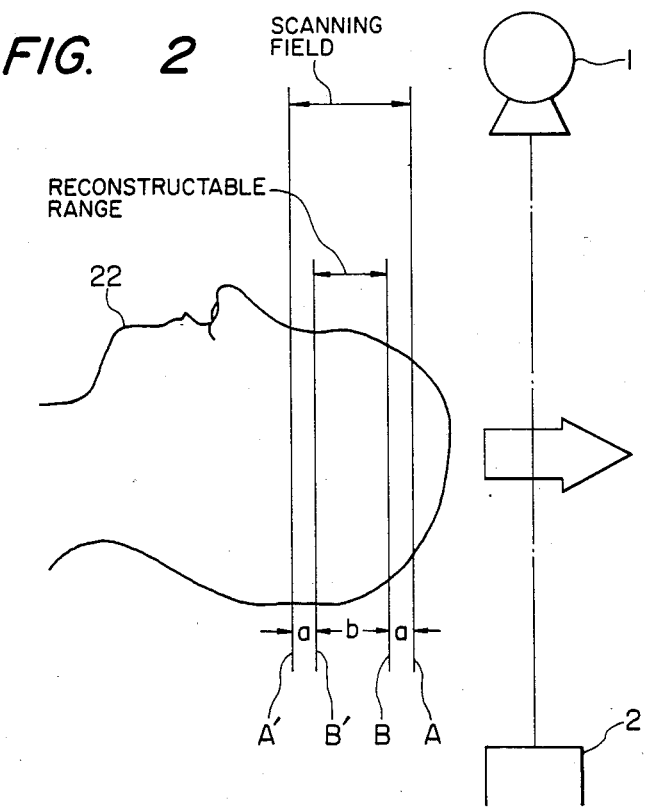
FIG. 2 shows a view for describing scan photographing steps.

The concrete steps of tomographic photography in accordance with the present invention are now described with reference to FIG. 2. The subject bed bearing a patient, who is the subject, is inserted into the gantry aperture and positioned, through the operation of a positioning light projector or the like, for the photographing. After that, the subject bed is pulled back by a distance (a) extending from the subject first photographed cross-section B which serves as a reference for the start of the photographing. The distance (a) is preset to provide a margin to increase the movement speed of the subject bed to a constant level by the time the cross-sectional plane B enters into the X-ray irradiation range.

While the subject bed is pulled back by the distance (a), the scanner is rotated to start the tomographic photography. When the rotation of the scanner reaches a constant speed, the subject bed is moved forward so that the speed of the movement of the bed becomes constant before the cross-sectional plane B is reached. The irradiation of the X-rays, which may be basically either pulsating or continuous, is started at the same time as the irradiated cross-section of the subject reaches the cross-sectional plane B. After the subject last photographed cross-section B' located at a distance (b) from the irradiation start plane B passes through the scanning plane, the irradiation of the X-rays is stopped and the subject bed is decelerated to be stopped at a cross-sectional plane A'. The distance (b) corresponds to the thickness of the subject imaginary slice upon which the X-rays are irradiated.

Figure 3:
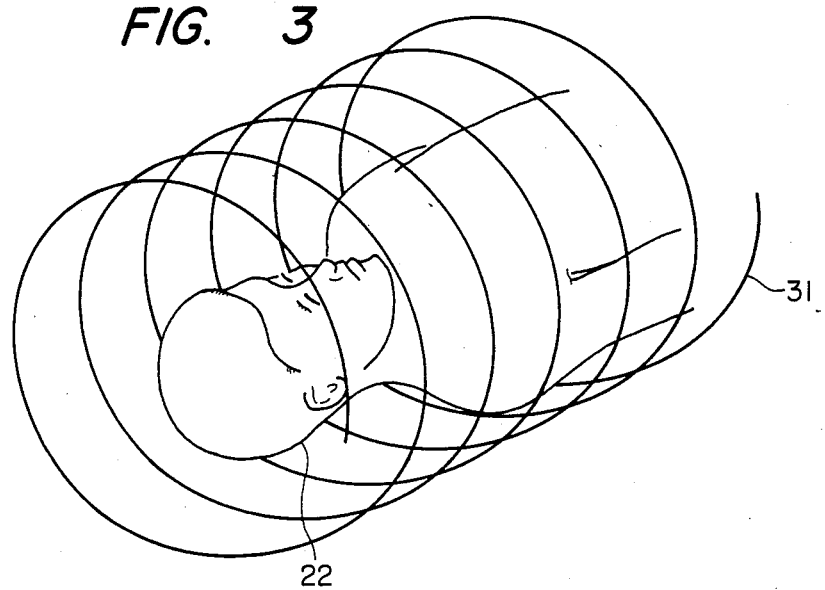
FIG. 3 shows a view indicating the spiral locus of an X-ray tube seen from a stationary subject.

The locus 31 of the X-ray tube during the movement of the subject bed in the scanning operation of the scanner looks spiral if viewed from the stationary subject 32, as shown in FIG. 3. Therefore, the scanning operation can be called spiral scanning.

Figure 4:
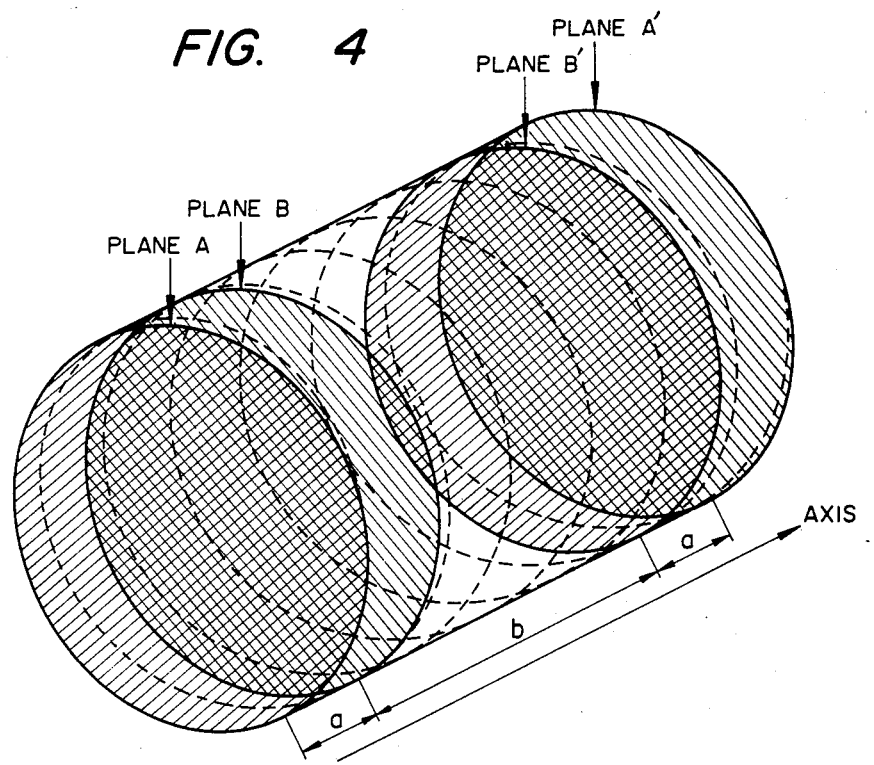
FIG. 4 shows a perspective view indicating the locus of the X-ray tube and cross-sections perpendicular to the axis of the subject throughout the period from the beginning of movement of the subject bed to the end thereof.

FIG. 4 shows a perspective view indicating the locus of the X-ray tube and the cross-sectional planes, A, B, B' and A' (perpendicular to the axis of the subject) during the period of the beginning of the movement of the subject bed to the end of the movement thereof.

It is necessary to note that the distance (b) for the photographed cross-section range includes a portion at which data of an angle range from 0 to $2\pi$ on one slice immediately behind a position corresponding to the beginning of measurement and those of an angle range from 0 to $2\pi$ on one slice immediately in front of a position corresponding to the end of the measurement, in the direction of the movement of the subject bed are handled only for interpolation to obtain projection data of actually reconstructable plane.

If the distance (b) is not set to include that portion but is set to correspond to only a tomogram reconstruction range, the distance (a) needs to be preset to be long enough to obtain measured data on not only the intermediate slices but also the slice immediately behind the position corresponding to the beginning of the measurement and that immediately in front of the position corresponding to the end thereof.

Figure 5:
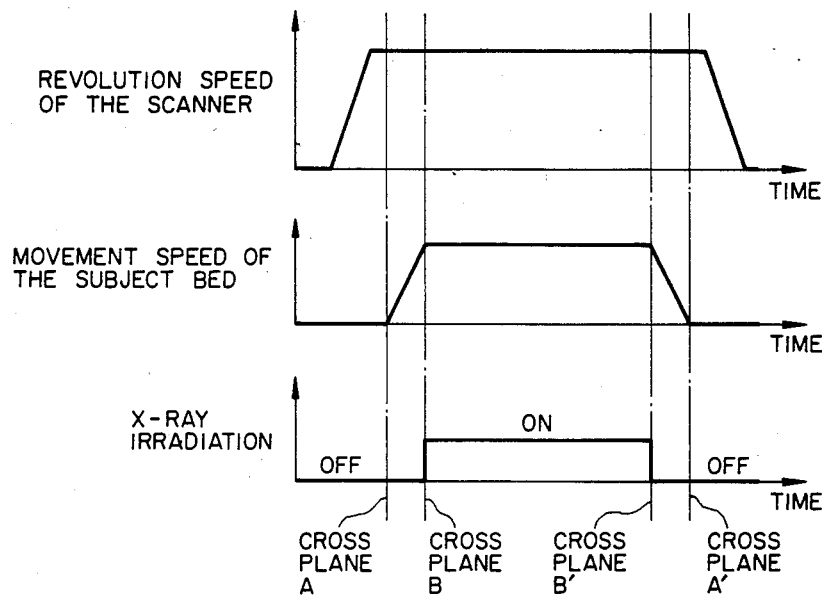
FIG. 5 shows time charts of the revolution speed of a scanner, the movement speed of the subject bed and the irradiation of X-rays with reference to photographed cross-sections.

FIG. 5 shows time charts of the revolution speed of the scanner, the movement speed of the subject bed and the irradiation of the X-rays with reference to the cross-sectional planes A, B, B' and A'. When the plane of rotary scanning by the scanner is coincident with the cross-sectional plane A, the rotation of the scanner is started. After the revolution speed of the scanner becomes constant, the subject bed is moved. When the movement speed of the subject bed becomes constant, the irradiation of the X-rays is started. The movement acceleration of the subject bed must be preset so that the start of the irradiation of the X-rays corresponds to the cross-sectional plane B. The irradiation of the X-rays is continued until the cross-sectional plane B' passes. After the cross-sectional plane B' passes, the irradiation of the X-rays is stopped. At the same time, the movement of the subject bed is decelerated so that the subject bed is stopped. After the stoppage of the subject bed, the rotation of the scanner is stopped.

Figure 6A:
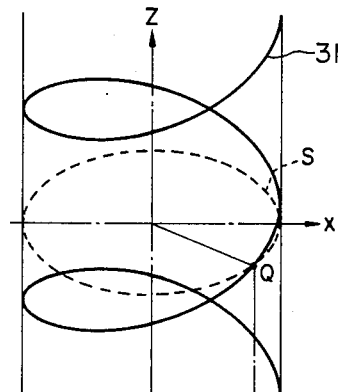
FIGS 6A and 6B show the relatioship between the spiral locus of the X-ray tube and the angle of projection.
Figure 6B:
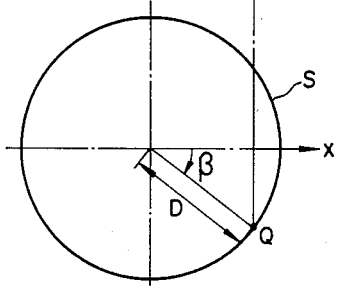

The relationship between the spiral locus of the X-ray tube and the projection angle of the spiral locus is shown in FIGS. 6A and 6B in preparation for the tomogram reconstruction calculation. As shown in FIG. 6A, the axis of the subject is the z-axis and two axes perpendicular to each other contained in the plane S perpendicular to the z-axis are the x-axis and the y-axis. FIG. 6A shows a plan view of the spiral locus of the X-ray tube seen downward along the y-axis perpendicular to the x-axis. An arbitrary cross-section perpendicular to the z-axis and the spiral locus of the X-ray tube intersect each other at only one point Q, which FIG. 6B shows as a point at projection angle $\beta$ (with reference to the x-axis) on the cross-section. FIG. 6B also shows the distance D between the center of the revolution of the X-ray tube and the focus thereof.

To reconstruct the tomogram of each cross-section, projection data located on the cross-section must be obtained. The spiral scanning is characterized in that it is substantially possible to reconstruct the tomogram of an arbitrary cross-section taken from within the range from a cross-section B corresponding to the start of photographing to a cross-section B' corresponding to the end of the photographing.

Figures 7A, 7B:
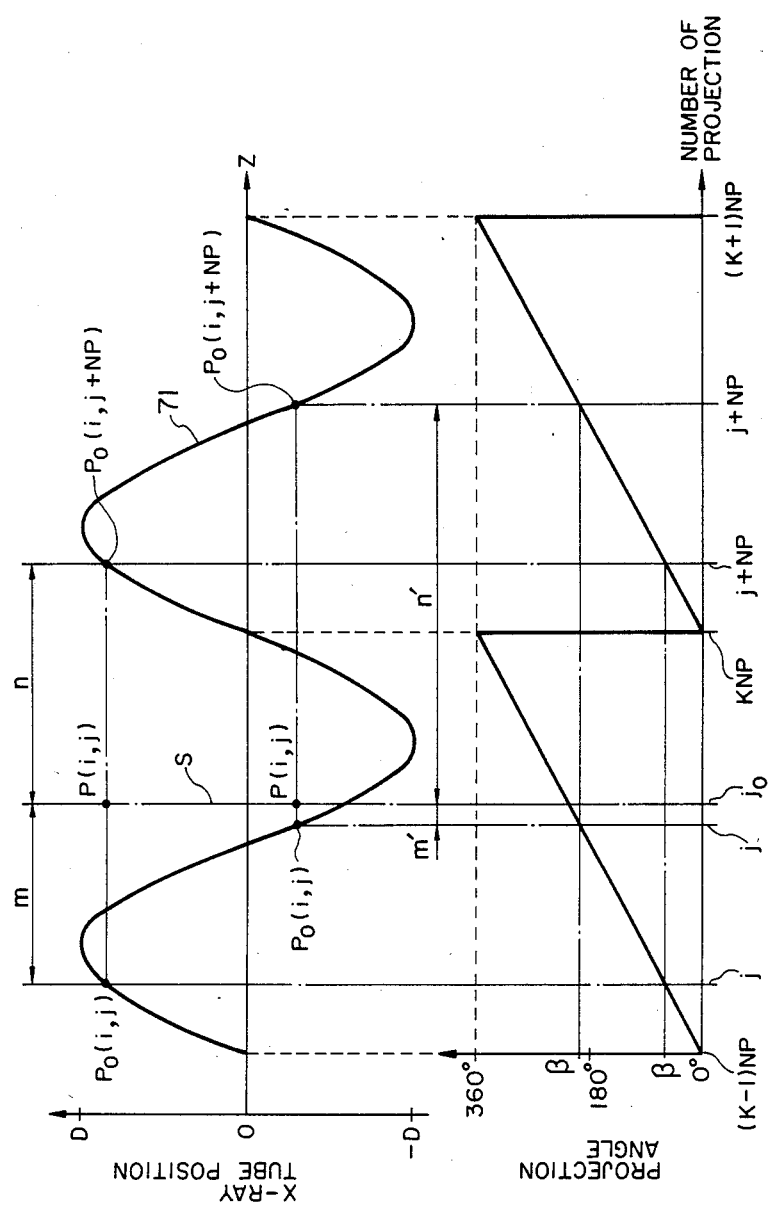
FIGS. 7A and 7B show the downward projection of the locus of the X-ray tube toward the subject and the relationship between the angle of the projection and the number of each view.

How to obtain the projection data on the arbitrary cross-section S is now described with reference to FIGS. 7A and 7B. FIG. 7A shows the downward projection 71 of the locus of the X-ray tube toward the subject. FIG. 7B shows the relationship between the projection angle and each projection number, that is, the number of pulsating irradiation or projection data acquisition from the beginning of measurement.

The projection data for the imaginary cross-section S in an arbitrary position is obtained in the following manner. The projection data to be obtained and former projection data measured by the spiral scanning are denoted by P(i, j) and Po(i, j), respectively. The symbols i and j denote the X-ray detector channel number and the projection number, respectively. If the projection data having the projection angle $\beta$ and corresponding to a position in front of the arbitrary cross-section S is expressed as Po(i, j), projection data having a projection angle $\beta+360°$ and corresponding to a position behind the cross-section S is expressed as Po(i,j +NP), where NP denotes the number of projections corresponding to one slice. The projection data P(i, j) on the cross-section S is therefore expressed by equation (1) through linear interpolation as follows.

$$P(i,j) = Po(i,j) \cdot n + Po(i,j+NP) \cdot m \quad (1)$$

i=1~CN  CN: number of all detector channels
j=1~NP  NP: number of all projections (360°)

In equation (1), symbols m and n denote interpolation coefficients which are independent of the original number of the channel and vary depending on the ordinal number j of the projection. The interpolation coefficients m and n are usually expressed by equations (2) as follows:

$$\begin{cases} m = (j_0 - j)/NP \\ n = 1 - m \end{cases} \quad (2)$$

In equations (2) a condition $j \leq J_0 \leq j+NP$ exists and jo denotes the number of projection data of the imaginary cross section for which is to be obtained.

The case of j=j' is also shown in FIGS. 7A and 7B in which K denotes a positive integer such that K>1.

To make the tomogram from the projection data obtained as described, deblurring filtration and back projection calculation are performed according to a filtered back projection method or the like to reconstruct the tomogram.

One of the tomogram reconstruction methods is a direct back projection method (1) in which deblurring filtration is performed in the same manner as the locus of a fan beam, directly on a two-dimensional image memory space expressed by a rectangular coordinate system. The other of the methods is an arrangement method (2) in which parallel beam projection data are created through reordering and rebinning calculations from a group of projection data obtained in a fan beam configuration beam and are then subjected to deblurring filtration to perform back projection calculation.

The direct back projection method is adopted in this embodiment.

For the projection data P(i, j) obtained by the equation (1), $\alpha$ and $\beta$ can be newly defined by equations (3) where up denotes the angle between the center lines of two X-ray detectors adjacent to each other when being viewed from the X-ray tube, and $\beta p$ denotes the interval of angle sampling in the measurement of projection data at every prescribed angle.

$$\begin{cases} \alpha = \alpha p \cdot i \\ \beta = \beta p \cdot j \end{cases} \quad (3)$$

If $\alpha p$ and $\beta p$ are small enough, $\alpha$ and $\beta$ can be regarded as continuous quantities, P(i, j) is then treated as P($\alpha, \beta$) below.

The projection data P($\alpha, \beta$) are first subjected to the deblurring filtration in accordance with equation (4) as follows.

$$Q(\alpha,\beta) = \int C(\alpha')H(\alpha')P(\alpha-\alpha',\beta)d\alpha' \quad (4)$$

In equation (4), C($\alpha$) denotes a correction term for unequal-interval sampling based on a geometrical system grounded on measurement with the use of the fan beam and can be approximately expressed by equation (5) as follows.

$$C(\alpha) = \cos(\alpha) \quad (5)$$

H($\alpha$) denotes a filter function for deblurring. The filter function is similar to the Shepp & Logan filter.

In calculation in the direct back projection method, by using the angle $\alpha\beta$ connecting X-ray source to coordinates (x, y) on the reconstruction plane and the measurement start angle, the angle α between X-ray beam through arbitrary coordinates (x, y) on the reconstruction plane and the line connecting the rotation center and X-ray focal spot, is expressed by equation (6) and (7) as follows.

$$\alpha = -\beta + \gamma \quad (6)$$

$$\gamma = \tan^{-1}\{(y - D \cdot \sin \beta)/(x - D \cdot \cos \beta)\} \quad (7)$$

A weight $L^2$ provided in consideration of the fact that the fan beam diverges as it goes away from the X-ray source is expressed by equation (8) as follows.
$$L^2 = (x - D \cdot \cos \beta)^2 + (y - D \cdot \sin \beta)^2 \quad (8)$$

The angle α and the weight $L^2$ determined as described above are used to perform cumulative addition as to all the coordinate points on the tomogram in accordance with equation (9) throughout an angle range of $\beta o + 2\pi$ from the measurement start angle $\beta o$ on the slice plane, the tomogram of which is to be made.

$$f(x,y) = \sum_{\beta=\beta_0}^{\beta=\beta_0+2\pi} (1/L^2) \cdot Q(\alpha,\beta) d\beta \quad (9)$$

In equation (9) $1/L^2$ denotes a weight for correcting a partial fan-beam effect in which the X-ray beam for the measurement diverges from the X-ray source toward the X-ray detectors.

Figure 8:
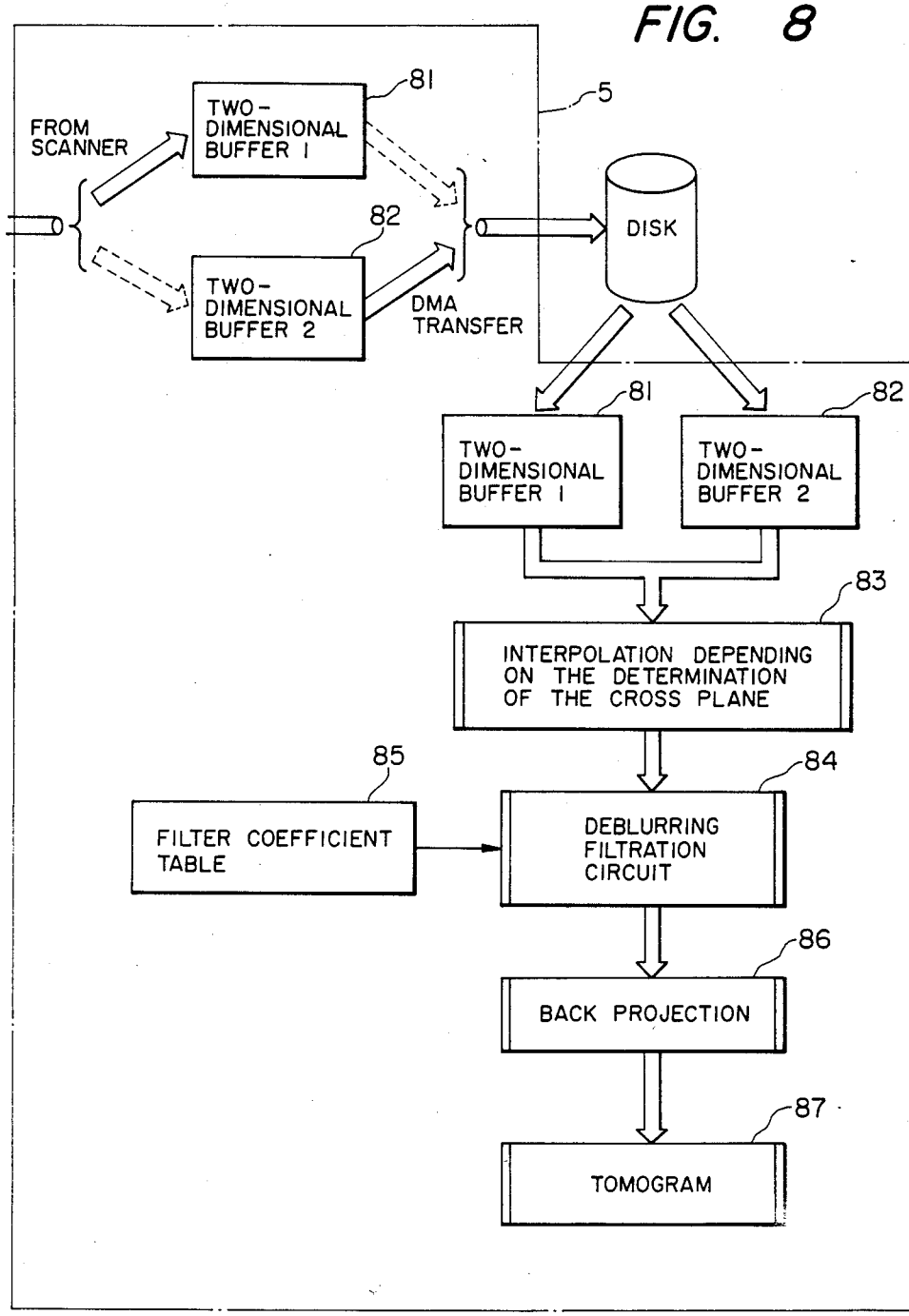
FIG. 8 shows an back projection calculating process.

The above-described back projection calculation process is summarized in FIG. 8.

Since the projection data P(α, β) are quantized with the sampling intervals αp and βp in the direction of the projection angle and in the direction of the detector channel, the arbitrary angle β is expressed by equation (10) where i denotes the channel number of detector and j denotes the projection number.

$$\beta = \beta_o + \beta p \cdot j = \beta(j) \quad (10)$$

Equation (10) is conditioned as follows.

$$NP = 2\pi/\beta p (j=0,1\ldots,NP-1)$$

Equation (9) is then given as equation (11) to express the discreteness with respect to j.

$$f(x,y) = \beta p \sum_{j=0}^{j=NP-1} (1/L^2) Q(\alpha,\beta(j)) \quad (11)$$

Since the detector channel angle α determined by the equations (6) and (7) with respect to the arbitrary coordinate point (x, y) on the tomogram does not necessarily coincide with the sampling point in the direction of detector channel, the reconstructed tomogram is obtained according to equation (12) if quadratic interpolation with four-nearby-points, for example, is used.

Since the detector channel angle determined by the equations (6) and (7) with respect to the arbitrary coordinate point (x, y) on the tomogram does not necessarily coincide with the sampling point in the direction of detector channel tomogram is obtained according 6 to equation (12) if quadratic interpolation with four nearby points, for example, is used.

$$f(x,y) = \alpha p \beta p \sum_{j=\Phi}^{j=NP-1} (1L^2) \sum_{n=-1}^{2} gn(\delta)Q\{\alpha(i+n),\beta(j)\} \quad (12)$$

In equation (12), gn(δ), denotes an interpolation function, and δ and i are as follows.

$$i = \}\alpha/\alpha p\{ \quad (13)$$

$$\delta = \alpha - \alpha p \cdot i \quad (14)$$

In equation (13), bracket denotes the Gaussian symbol.

When the above-described treatment is performed as to all the coordinate points on the tomogram, the back projection calculation is completed. The number of all the times of the back projection calculation is equal to the product of the number of pixels and that of the projections. The completion is done when calculations are made in accordance with equations (6), (7), (8), (12), (13) and (14) the same number of times as the product.

The operation of the tomograph reconstruction is now described with reference to FIG. 8. The tomogram can be reconstructed while the projection; data is collected by a system which performs the spiral scanning. Since the interpolation needs to be performed in the direction of movement of the subject's bed as descried above, two buffers (each of which is a two-dimensional memory for storing projection data for an angle range of 360°) are provided so that projection data for one round of revolution of the scanner can always be kept in addition; to other projection data. The tomogram reconstructing calculation cannot be performed until the projection data for one round of rotation of the scanner is collected to execute the interpolation. However, after the projection data for one round of rotation of the scanner is collected, the interpolation can be performed between the projection data stored in one of the buffers and that being currently collected, along with the storage of the already collected projection data into the other buffer, so that the tomogram is reconstructed. When the collection of the projection data for one buffer is finished, the tomogram reconstructing calculation is terminated and the tomogram of one cross-section is completed. Subsequently, the contents of the other buffer for the preceding cross-section are allowed to be removed therefrom. Therefore, new projection data is stored into the buffer and interpolation is simultaneously performed between the new projection data and projection data on another cross-section so that another tomogram can be reconstructed. A series of such operations is sequentially performed so that a tomogram can be reconstructed at every round of rotation of the scanner.

Such a tomogram is usually stored in a displaying memory. If two displaying memories are provided, a previously made tomogram can be stored onto a disk by DMA transfer during the reconstruction of a subsequent tomogram so that the tomogram stored in the disk can be read out therefrom. However, such a method provides a disadvantage in that the reconstruction of a tomogram is confined to an imaginary slice for one period of operation; of the scanner. On the other hand, the spiral scanning provides an advantage that the tomogram of an arbitrary cross-section can be obtained. For that reason, the description of the tomograph is hereafter performed on the assumption that it has a projection data collection mode and a tomogram reconstruction mode.

In the projection data collection mode, the use of each of the buffer, each of which keeps the projection data obtained in one scanning (for an angle range of 360° or one round of rotation of the scanner), are changed with one another at the end of each scanning. When the tomographic photographing is started, the collected projection data is stored into two-dimensional buffer 81 in accordance with the sequence of the numbers of channels and that of the numbers of projections. When one scanning is terminated, the storage of projection data is switched to the other two-dimensional buffer 82. The contents of the buffer 81 are then stored into the disk by DMA transfer during the storage of the projection data into the other buffer 82. When another scanning is terminated, the buffers 81 and 82 are changed for each other again. In other words, collected projection data are stored into buffer 81, and the contents of the other buffer 82 are stored into the disk by DMA transfer. Buffer 81 and 82 are thus changed with each other in the storage of projection data so that the projection data sequentially allocated to the buffers in each scanning are present on the disk in accordance with the sequence of the channel numbers, the projection numbers and the scanning numbers at the end of all of the scannings.

When the projection data collection mode is terminated, the tomogram reconstruction mode is started. At that time, a cross-section, the tomogram of which is to be reconstructed, is first determined. The projection data in two scannings performed in angle ranges of $\pm 2\pi$ from the angle of the projection corresponding to the determined cross-section are stored into both of two dimensional buffers 81 and 82 from the disk in which the projection data in all the scannings are sequentially stored. The projection data in the same addresses in buffers 81 and 82 are entered into circuit 83 which functions to perform interpolation depending on the determined cross-section to create projection data in accordance with the first and the second equations (1) and (2). Deblurring filtration circuit 84 sequentially performs deblurring correction on the created projection data in accordance with filter coefficient circuit 85. The data is then subjected to back projection by back projection calculating circuit 86 to make tomogram 87.

Figure 14:
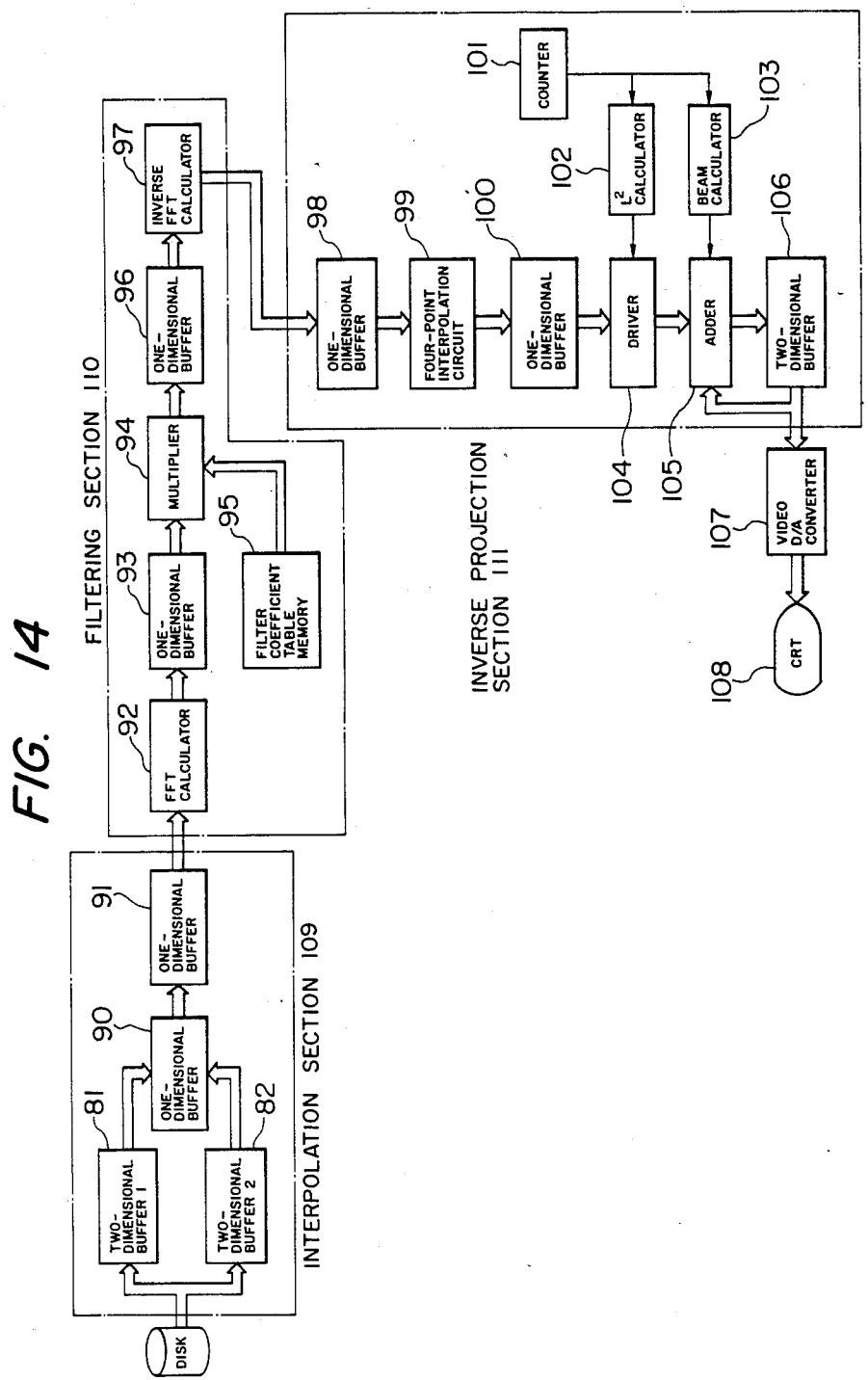
FIG. 14 shows a concrete constitution of hardware according to an embodiment of the present invention.

The concrete hardware constitution of the first embodiment is now described with reference to FIG. 14. As described above, the projection data obtained in the projection data collection mode are stored in accordance with the sequence of the channel numbers, the projection numbers and the scanning numbers. To perform the interpolation in accordance with the first and the second equations (1) and (2), the desired cross-section is selected and the data corresponding to the desired cross-section are stored into both of the two-dimensional buffers 81 and 82 by DMA transfer. Since the contents of buffers 81 and 82 are previously stored into them in sequences appropriate to the interpolation in the direction of the movement of the subject or Z axis, equation (1) can be directly used if the data in the same addresses in both the buffers are read out therefrom. The interpolation is performed by interpolation circuit 90. The result of the interpolation is transferred to one-dimensional buffer 91. The extension including two-dimensional buffers 81 and 82, interpolation circuit 90 and one-dimensional buffer 91 is herein referred to as interpolation section 109.

Ordinary tomogram reconstructing calculation is then performed. The contents of one-dimensional buffer 91 are subjected to Fourier transformation by FFT (fast Fourier transformation) calculator 92 so that the contents are converted to the frequency domain. The result of the conversion is stored into one-dimensional buffer 93. The contents of buffer 93 and those of filter coefficient table memory 95, in which the result of creation of the product of the values of equation (5) and a filter function for deblurring correction is stored, are multiplied together by multiplier 94 to obtain one-dimensional data which are stored into one-dimensional buffer 96. Since the one-dimensional data is a result of calculation in the frequency domain, the data is converted to the real space domain by inverse FFT calculator 97. The result of the conversion is stored into a one-dimensional buffer 98. The extension including FFT calculator 92, one-dimensional buffer 93, multiplier 94, memory 95, one-dimensional buffer 96 and inverse FFT calculator 97 is herein referred to as filtering section 110.

Four-point interpolation circuit 99 performs four-neareby-point interpolation on the contents of one-dimensional buffer 98, depending on the deviation of the path of the X-ray beam from the center of the X-ray detector. The result of the interpolation is stored into one-dimensional buffer 100. In compliance with a command from counter 101, the value $L^2$ corresponding to the coordinates (x, y) on the two-dimensional tomogram is computed by $L^2$ calculator 102 according to equation (8). The value of the contents in one-dimensional buffer 100 is divided by the value $L^2$ in divider 104. The result of the division and the value of the contents previously stored in two-dimensional buffer 106 are added together by adder 105 according to a command from beam calculator 103. Such steps are taken for all projection angles to obtain the desired tomogram. Data on the tomogram is displayed on cathode-ray tube 108 through video D/A converter 107 so that the tomogram is visible. The extension including one-dimensional buffer 98, four-point interpolation circuit 99, one-dimensional buffer 100, counter 101, $L^2$ calculator 102, beam calculator 103, divider 104, adder 105 and two dimensional buffer 106 is herein referred to as inverse projection section 111.

Figure 9:
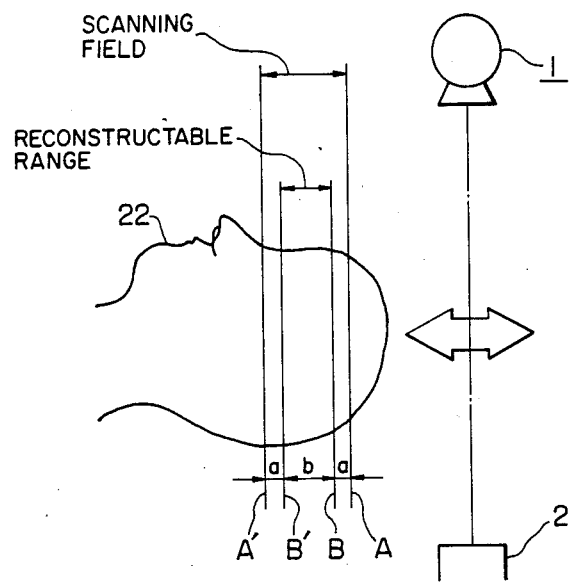
FIG. 9 shows steps of tomographic photographing by forward and backward scannings.

The second embodiment of the present invention is hereafter described. In this embodiment, a subject bed is moved not only forward as shown in FIG. 2 but also backward from a cross plane B' to another B as shown in FIG. 9, to perform scanning. There are two possible cases, in one of which the locus of the X-ray tube in the backward movement intersects that of the X-ray tube in the forward movement and in the other of which the locus of the X-ray tube in the backward movement does not intersect that of the X-ray tube in the forward movement. The second embodiment is described on the assumption that the loci of the X-ray tube in the forward and backward movements of the subject bed do not intersect each other.

Figure 10A:
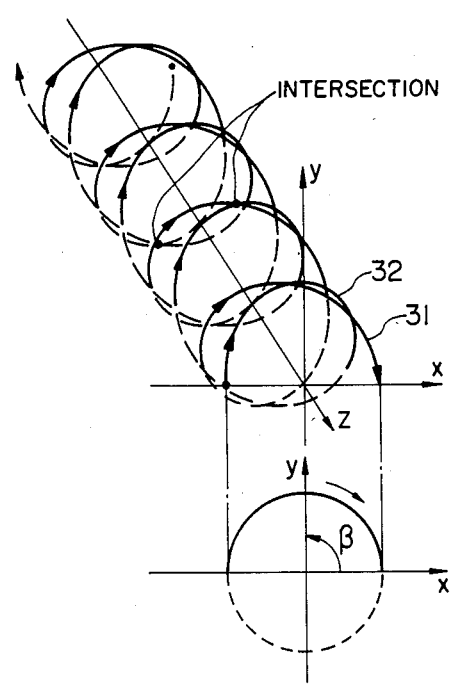
FIGS. 10A and 10B show the spiral locus of an X-ray tube seen from stationary subject in the forward and the backward scannings.
Figure 10B:
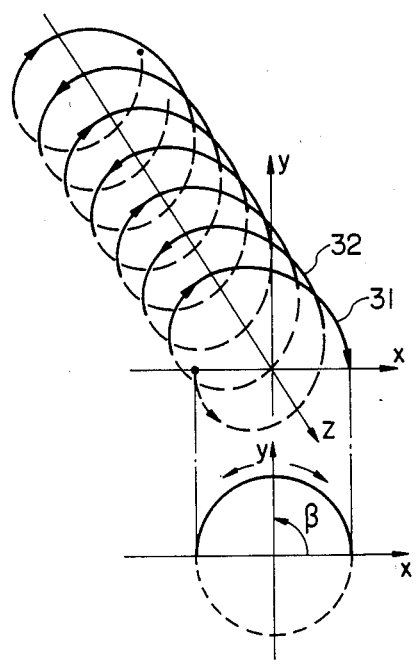

When a scanner is rotated opposite to the forward scanning direction to perform backward scanning, subject 32 is spirally scanned as shown in FIG. 10A. Locus 31 of the X-ray tube in the forward scanning and locus 32 of the X-ray tube in the backward scanning are measured such that both the loci extend along each other in the direction of the movement of the subject. The axis of the subject is referred to as the z-axis, and two axes perpendicular to each other contained in plane S perpendicular to the z-axis are referred to as the x-axis and the y-axis, in the same manner as those shown in FIG. 6. The loci of the X-ray tube in the forward and the backward scannings do not extend through the same point in a space (x, y, z). In FIGS. 10A and 10B solid lines showing the loci of the X-ray tube indicate that the X-ray tube is in an angle range from 0 to $\pi$, and dotted lines showing the loci indicate that the X-ray tube is in an angle range from $\pi$ to $2\pi$.

Figure 11:
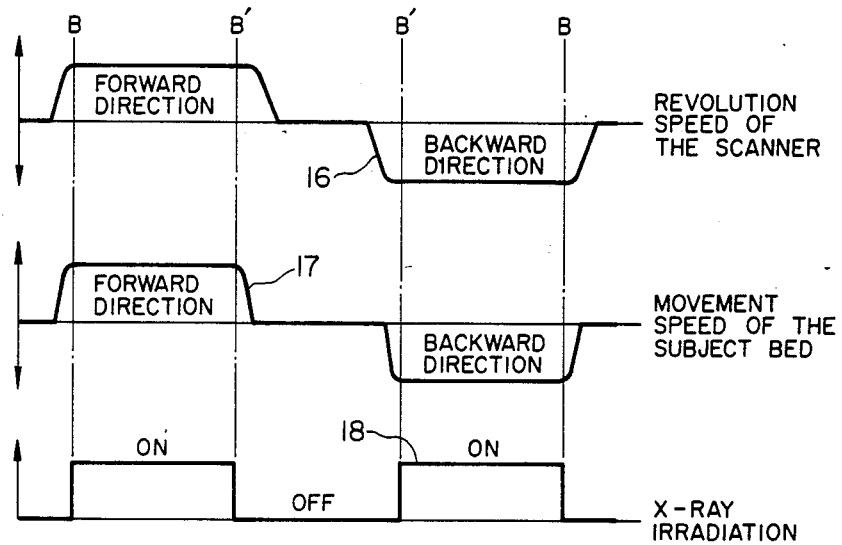
FIG. 11 shows time charts of the revolution speed of a scanner, the movement speed of the subject bed and the irradiation of X-rays with reference to photographed cross-sections in the forward and backward scannings.

FIG. 11 shows time charts of the revolution speed of the scanner, the movement speed of the subject bed and the irradiation of X-ray as to the forward and backward movements of the subject bed in the second embodiment. The scanner is first rotated. When the speed of the rotation of the scanner becomes constant, the subject bed is moved forward. When the speed of the movement of the subject bed becomes constant and a reference point passes through the cross-sectional plane B, the irradiation of the X-ray is started. When scanning from the cross-sectional plane B to the other B' is finished, the irradiation of the X-rays is stopped and the rotation of the scanner and the movement of the subject bed are halted. After that, the scanner is rotated backward, and the subject bed is moved backward. The rotation speed of the scanner and the movement speed of the subject bed are then made constant before the referenced point reaches the cross-sectional plane B'. When the reference point passes through the cross-sectional plane B', the irradiation of X-rays is started. The movement of the subject bed is synchronized with the revolution of the X-ray tube by previous adjustment so that the position of the X-ray tube on the cross-sectional plane B' in the forward scanning direction and that of the X-ray tube on the cross-sectional plane B' in the backward scanning direction are exactly opposite each other across an angle of 180°. When the reference point has passed through the cross-sectional plane B during the backward movement of the subject bed, the irradiation of the X-rays is stopped and the movement of the subject bed and the rotation of the scanner are halted.

Since the position of the X-ray tube during the forward movement of the subject bed and that of the X-ray tube during the backward movement of the subject bed are opposite to each other across the angle of 180° as described above, projection data obtained during the forward movement and those obtained during the backward movement are supplementary to each other if measurement for obtaining the projection data is performed by an offset detection unit, the center of an X-ray detector array of which is distant by a quarter of the width of each detector from a straight line extending from the center of the X-ray tube to that of the revolution of the X-ray tube. Roughly speaking, the X-ray beam for obtaining the projection data during the forward movement of the subject bed and that for obtaining the projection data during the backward movement of the subject bed overlap each other by one-half. For that reason, tomographic processing can be performed with high resolution.

The accuracy of interpolation for tomographic determination in the direction of movement of the subject bed is not only two times as high in the second embodiment than in the first embodiment but also the accuracy of the interpolation for tomographic determination in the direction of X-ray detector channel is increased in the second embodiment as compared with the first embodiment. Therefore, higher spatial resolution is achieved in the second embodiment. For that reason, the operation of the second embodiment can be called high-resolution processing in the spiral scanning system.

Figure 12:
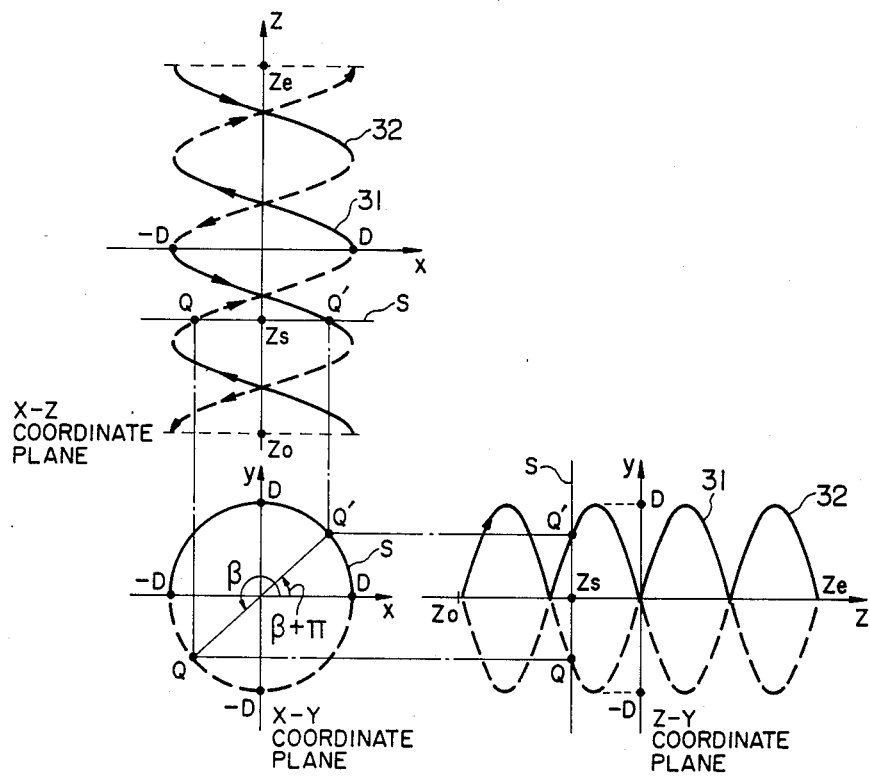
FIG. 12 shows the relationship between the spiral locus of the X-ray, tube and the angle of projection in the forward and the backward scannings.

The relation between the spiral locus of the X-ray tube and the projection angle is shown in FIG. 12 in the preparation for tomographic reconstructing calculation by the high-resolution processing in the spiral scanning system. FIG. 12 shows an x-y coordinate plane, an x-z coordinate plane and a z-y coordinate plane on the assumption that the axis of the subject is the z-axis and the two axes perpendicular to each other contained in the plane S perpendicular to the z-axis are the x-axis and the y-axis as shown in FIG. 6. Shown at 31 and 32 in FIG. 12 are the locus of the X-ray tube in the forward scanning direction and that of the X-ray tube in the backward scanning direction, respectively. Solid lines showing the loci 31 and 32 in FIG. 12 indicate that the X-ray tube is in an angle range from 0 to $\pi$. Dotted lines showing the loci 31 and 32 in FIG. 12 indicate that the X-ray tube is in the angle range from $\pi$ to $2\pi$. Shown at D in FIG. 12 is the distance between the focus of the X-ray tube and the center of the revolution thereof.

An arbitrary cross plane S perpendicular to the z-axis intersects the spiral loci 31 and 32 of the X-ray tube only at points Q and Q'. When the points Q and Q' are shown on the x-y coordinate plane, the points have projection angles $\beta$ and $\beta + \pi$, respectively, with reference to the x-axis. In other words, points Q and Q' have a projection angle difference of 180°. For this reason, the high-resolution processing can be performed by using the offset detection unit.

The reconstruction of the tomogram of an arbitrary cross-section in a range from a cross-section positioned behind a position corresponding to the beginning of tomographic photographing to a cross-section positioned in front of a position corresponding to the end of the tomographic photographing can be substantially performed through the spiral scanning as described above. Therefore, the projection data obtained through the spiral scanning can be defined by the angle $\alpha$ in the direction of detector channel, the projection angle $\beta$ and the position $\alpha$ in the direction of the movement of the subject so as to be expressed as $p(\alpha, \beta, Z)$. To reconstruct the tomogram in an arbitrary position Zs in the direction of z-axis, the projection data $P(\alpha, \beta$ Zs) on the cross-section in the position Zs must be obtained. The projection angle $\beta$ and the position Z can be expressed as follows.

$$\beta = \beta o + \Delta \beta * j \quad (15)$$

$$Z = Zo + \Delta Z * j (j=0,1,2,\ldots,Nt-1) \quad (16)$$

In equations *15) and (16), denotes the interval of angle sampling, $\Delta Z$, the length of the movement of the subject bed during the revolution of the X-ray tube through the interval $\Delta \beta$, j, the number of each projection, $\beta o$, the projection angle at the start of the irradiation of the X-rays in the forward scanning, Zo, the position of the imaginary slice at the start of the irradiation of the X-rays and NP, the number of all the measurement projections.

As for the projection data obtained in the backward scanning direction, the projection angle $\beta r$ in the slice position Z expressed by equation (16) is expressed as follows.

$$\beta r = \beta + \pi \quad (17)$$

FIG. 13A shows a z-y coordinate plane. FIG. 13B shows graphs with the abscissa axis for the projection number along the z-axis and with the ordinate axis for the projection angle $\beta$. The projection number Js corresponding to the imaginary slice position Zs is expressed in terms of equation (16) as follows.

$$Js=(Zs-Zo)/\Delta Z$$

Projection data to be obtained, those obtained in the forward spiral scanning direction and those obtained in the backward spiral scanning direction are then expressed using the projection number corresponding to the position in Z direction as (P$\alpha$, $\beta$, j), P1($\alpha$, $\beta$, j1) and P2($\alpha$, $\beta$, j2).

For that reason, the projection data P($\alpha$, $\beta$, Js) on the cross plane S, that at the position of projection number Js corresponding to the position Zs in the forward spiral scanning, can be obtained by linear interpolation according to equation (30).

$$\begin{cases} P(\alpha,\beta,Js) = P1(\alpha,\beta,j1)n + P2(\alpha,\beta,j2)m \\ j1 = Js - NP/2 + k \\ \beta = \beta_0 + \Delta\beta \cdot k \\ \alpha = a_p * l \end{cases} \quad (30)$$

$l = 0, 1, 2, 3, \ldots, CN - 1 \quad$ CN: number of all channels
$k = 0, 1, 2, 3, \ldots, NP - 1 \quad$ NP: number of projection at angle range from 0 to $2\pi$ Symbols m and n above denote interpolation coefficient which are independent of $\alpha$ but vary depending on the projection number j. The interpolation coefficient m and n are usually expressed by equation (31) as follows.

$$\begin{cases} m = |(j1 - Js)/(NP/2 - 1)| \\ n = 1 - m \end{cases} \quad (31)$$

where | | means the absolute operation. And, j2 is expressed by equation (32) at each conditions.

$$j2 \begin{cases} j1 + NP/2, Js \geq j1 \\ j1 - NP/2, Js < j1 \end{cases} \quad (32)$$

Start projection angle $\beta o$ is expressed in this embodiment as follows.

$$\beta o = \Delta\beta \cdot (Js - NP/2) \quad (33)$$

Such treatment is performed on the projection "data" obtained through the use of the quarter offset detection unit, so that the projection data for reconstructing the high-resolution tomogram of the cross-section S is obtained.

To make the high-resolution tomogram on the basis of the projection data obtained as described above, deblurring filtration and back projection calculation are performed according to the filtered back projection method or the like to execute reconstruction as described for the first embodiment.

The third embodiment of the present invention, in which the loci of an X-ray tube in forward and backward scannings intersect each other, will now be described. When a scanner is rotated in the same direction so as to perform the backward scanning, the loci of the x-ray tube in the forward and the backward scannings intersect each other as shown in FIG. 10B, and subject is spirally scanned. Solid lines showing the loci of the X-ray tube in FIG. 10B indicate that the X-ray tube is in an angle range from 0 to $\pi$. Dotted lines showing the loci of the X-ray tube in FIG. 10B indicate that the X-ray tube is in an angle range from $\pi$ to $2\pi$.

Figure 16:
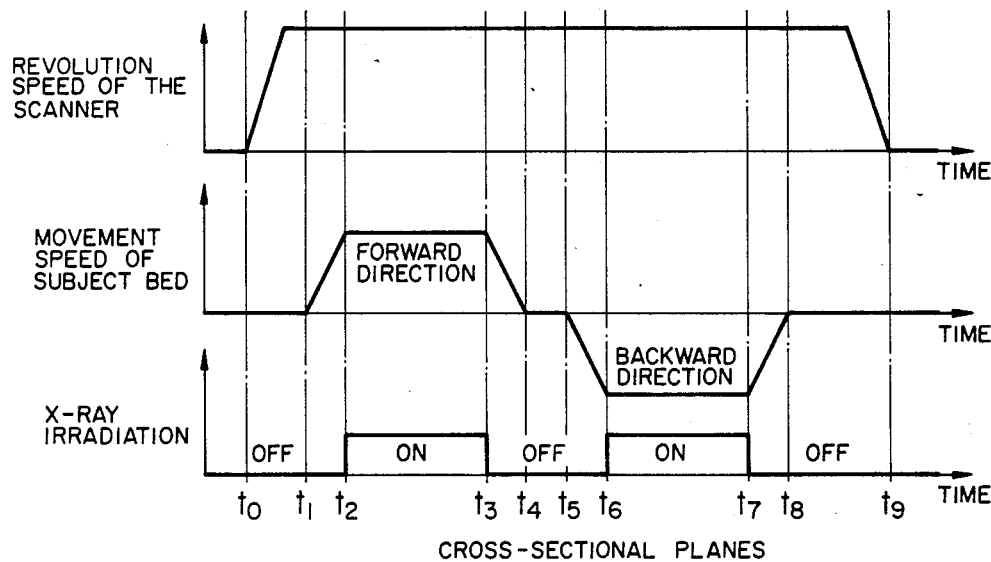
FIG. 16 shows time charts of the revolution speed of a scanner, the movement speed of the subject bed and the irradiation of X-rays with reference to photographed cross-sections in the forward and backward scannings.

FIG. 16 shows time chart of the revolution speed of the scanner, the movement speed of a subject bed and irradiation of X-rays in the forward and backward movements of the subject bed. The scanner is first rotated. When the revolution speed of the scanner becomes constant, the subject bed is moved forward. When the movement speed of subject bed becomes constant and a reference point has passed through a cross-sectional plane B, the irradiation of the X-rays is started. After scanning from the cross-sectional plane B to another cross-sectional plane B' is completed, the irradiation of the X-rays is stopped and subject bed is halted. The scanner is continuously rotated at this period. After that, the subject bed is moved backward so that the movement speed thereof becomes constant before the cross-sectional plane B' reaches the scanning plane, the irradiation of X-rays is started. The movement of the subject bed must be synchronized with the revolution of the X-ray tube by previous adjustment so that the position of the X-ray tube on the cross-sectional plane B' in the forward scannag direction and that of the X-ray tube on the cross-sectional plane B' in the backwardscanning direction are exactly opposite each other across an angle of $\pi$. When the cross-sectional plane B passes through the scanning plane during the backward movement of the subject bed, the irradiation of the X-ray is stopped and the movement of the subject bed and rotation of the scanner are halted.

Since the direction of the scanner rotation is the same for both forward and backward scanning in the third embodiment, the backward scanning can be started without once stopping rotation of the scanner. Shown in FIG. 16, the time point to is the starting time of the scanner rotation, t1, the starting time of subject bed movement in forward scanning, t2, the starting time of the X-ray irradiation in forward scanning, t5, the starting time of subject bed movement in backward scanning and t6 is the starting time of the X-ray irradiation in backward scanning. Although the time t2 - t1, t4 - t3, t6 - t5, t8 - t7 required acceleration or deceleration of the subject bed can be predetermined, the time t5 - t4 from the end of the forward scanning to the beginning of the backward scanning must be adjusted to synchronize the movement or the subject bed and the scanner rotation with each other. Because the position of the X-ray tube at the time point t6 of the irradiation of the X-rays upon the cross-section B' in the backward scanning must be completely opposite to that of the X-ray tube in the forward scanning. For the purpose, a relation expressed by equation (20) where $\omega$ denotes the angular velocity of the revolution of the X-ray tube and K denotes a positive integer must exist.

$$(2K+1)\pi = \omega(t6-t3) \quad (20)$$

As a result, the subject bed stoppage time $t5-t4$ can be determined according to equation (21) as follows.

$$t5-t4=(t6-t3)-(t4-t3)-(t6-t5)=(2K+1)\pi/\omega - (t4-t3)-(t2-t1) \ldots \quad (21)$$

In equation (21), t4 t3 and t2 t1 denote previously measure values.

The relationship between the spiral locus of the X-ray tube and the projection angle is shown in FIG. 15 in preparation for tomogram reconstructing calculation. FIG. 15 shows an x-y coordinate plane, an x-z coordinate plane and a z-y coordinate plane on assumption that the axis of the subject is a z-axis and two axes perpendicular to each other contained in a plane S perpendicular to the z-axis are an x-axis and a y-axis, in the same manner as those shown in FIG. 6. Shown at 31 in FIG. 15 is the locus of the X-ray tube in backward scanning. Solid lines showing the loci 31 and 32 in FIG. 15 indicate that the X-ray tube is in an angle range from 0 to $\pi$. Dotted lines showing the loci 31 and 32 in FIG. 15 indicate that the X-ray tube is in an angle range from $\pi$ to $2\pi$. Shown at D in FIG. 15 is distance between the focus of the X-ray tube and the center of the scanner rotation. An arbitrary cross plane S intersects the spiral loci 31 and 32 of the X-ray tube only at points Q and Q'. When the points Q and Q' are shown on the z-y coordinate plane, the points have projection angles $\beta$ and $\beta'$, respectively, with reference to the x-axis.

The projection angle $\beta$ and position Z can be expressed by equations (15) and (16) where $\Delta\beta$ denotes the interval of angle sampling, $\Delta Z$, the length of the movement of the subject bed during the revolution of the X-ray tube through the interval $\Delta\beta$, j, the number of projection, $\beta o$, the projection angle at the start of the irradiation of the X-rays in the forward scanning and Zo, the position of the imaginary slice at the start of the irradiation of the X-rays.

Figure 17:
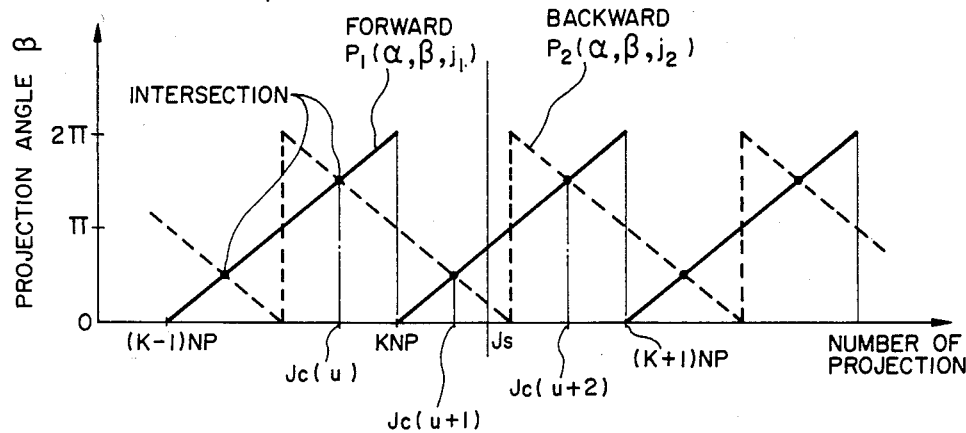
FIG. 17 shows the relationship between the angle of the projection and the number of each projection in the forward and the backward scannings.

FIG. 17 shows the graph with the abscissa axis for the projection number along the z-axis and with the ordinate axis for the projection angle $\beta$, in the same manner as those shown in FIG. 14B. The projection number Js corresponding to the slice position Zs shown in FIG. 15 is expressed in terms of equation (16) as follows.

$$Js=(Zs-Zo)/Z \quad (22)$$

Projection data obtained in the spiral scanning can be defined by the angle $\alpha$ in the direction of detector channel, the projection angle $\beta$ and the position Z in the direction of the juxtaposition of imaginary slices of the subject so as to be expressed as $P(\alpha, \beta, Z)$. To reconstruct the tomogram of the cross-section in a position Zs in the direction of juxtaposition of imaginary slices of the subject, the projection data $P(\alpha, \beta, Zs)$ on the cross-section in the position Zs must be obtained.

The position Zc(u) of the intersection of loci of the forward and backward scannings is expressed by equation (40).

$$Zc(u)=Zo+NP/4*\Delta Z+NP/2*\Delta Z*u \ (u=0,1,2,\ldots,2K-1) \quad (40)$$

A symbol Zo above denotes the start position of irradiation in the direction of z-axis. And, a symbol u denotes a positive integer less than $2K-1$ where the scanner rotated K times for scanning subject. The projection number Jc(u) corresponding to the position of intersection Zc(u) is expressed by equation (41).

$$Jc(u)=j_o+NP/4+NP/2*u \quad (41)$$

The projection number Jc(u) is expressed as follows when the start projection number Jo of irradiation can be assumed by Jo=0, $$Jc(u)=NP/4+NP/2*u=NP(1+2u)/4 \ (u=0,1,2,\ldots,K-1)$$

The projection data in angle from $\beta o$ to $\beta o+\pi$ of a position Js between two intersections adjacent each other, $$Jc(u)<Js<Jc(u+1) \quad (42)$$

is obtained by equation (43). The projection data obtained in the forward and backward spiral scannings is expressed as $P1(\alpha, \beta, j1)$, $P2(\alpha, \beta, j2)$.

$$p(\alpha,\beta,Js) = p1(\alpha,\beta,j1)n + p2(\alpha,\beta,j2)m \quad (43)$$

$$\begin{cases} j1 = Jc(u) + k \\ j2 = \begin{cases} Jc(u+2) - k, & j1 < Js \\ Jc(u) - k, & j1 > Js \end{cases} \end{cases}$$

$$(k = 0, 1, 2, \ldots, NP/2 - 1)$$

The projection data $P(\alpha, \beta, Js)$ in an angle range from $\beta o$ to $\beta o - \pi$ is obtained by equation (44).

$$p(\alpha,\beta,Js) = p(\alpha,\beta,j1)n + p2(\alpha,\beta,j2)m \quad (44)$$

$$\begin{cases} j2 = Jc(u) + k \\ j1 = \begin{cases} Jc(u+2) - k, & j1 < Js \\ Jc(u) - k, & j1 > Js \end{cases} \end{cases}$$

$$(k = 0, 1, 2, \ldots, np/2 - 1)$$

In equations (43) and (44), the interpolation coefficient m and n are obtained by equation (45).

$$\begin{cases} m = |(Js - j1)/(j1 - j2)| \\ n = 1 - m \end{cases} \quad (45)$$

where $|\ |$ denotes the absolute operation.

The tomogram of an arbitrary cross-section can be substantially made by the spiral scanning. The projection data of the cross plane including intersection of loci of the forward and the backward scannings is obtained easily in third embodiment. The projection data $P(\alpha, \beta, Js)$ can be obtained by equation (46) where the position Js is Jc(u).

$$\begin{cases} P(\alpha,\beta,Js) = (P1(\alpha,\beta,j1) + P2(\alpha,\beta,j2))/2 & (46) \\ j1 = Jc(u-1) + k & (47) \\ j2 = Jc(u+1) - k \quad (k = 0, 1, 2, \ldots, NP-1) \end{cases}$$

The spiral scanning of third embodiment is characterized in that the cross-section in the position of intersection of loci of forward and backward scannings is obtained in the terms of equations (46) and (47) easily.

To reconstruct the high-resolution tomogram on the basis of the projection data obtained as described above, deblurring correction filtering and back projection calculation are performed in the filtered back projection method or the like to execute reconstruction, as described for the first embodiment.

To make high-resolution tomogram on the basis of the projection data obtained as described above, deblurring correction filtering and back projection calculation are performed in the filtered back projection method or the like to execute reconstruction, as described for the first embodiment.

Although the invention has been described with reference to particular means, methods, embodiments, it is to be understood that the invention is not confined to the embodiment described in the foregoing and illustrated herein, but extends to all equivalents within the scope of the claims.

For example, although it has been described in the foregoing description to obtain data of a slice of the subject, the plane of which being perpendicular to the z-axis, it is further possible to obtain data of obliquely sliced plane of the subject.

What is claimed is:

1. A computerized tomography system which includes an X-ray generator for producing X-rays, an X-ray detector array for detecting the X-rays transmitted through a subject, and a subject bed, said X-ray tube and said X-ray detectors being opposed to each other, X-ray beams being irradiated upo said subject in a sectorial manner at a large number of angles to scan said subject while said X-ray tube and said X-ray detectors are being revolved around said subject, said X-ray tube and said X-ray detectors remaining opposed to each other during the revolution, said system comprising:

means for rapidly and continuously revolving a frame bearing said X ray tube;

means for moving said subject bed perpendicularly to a plane of revolution of said X-ray tube and for moving said subject bed synchronously with the revolution of said X-ray tube;

means for scanning said subject along with the movement of said subject bed in a spiral with respect to a coordinate system positioned about an imaginary axis passing through said subject; and means for obtaining a reconstructed tomogram of an arbitrary cross-section within a range from a position corresponding to a beginning of the spiral scanning to a position corresponding to an end of the spiral scanning.

2. The computerized tomography system according to claim 1, further comprising means for performing the spiral scanning along with forward and backward movement of said subject bed.

3. The computerized tomography system according to claim 2 further comprising means for performing an adjustment so that the locus of said X-ray tube in forward movement of said subject bed and that of said X-ray tube in backward movement of said subject bed do not intersect with one another and data obtained during said backward movement comes in between two mutually adjacent data previously obtained during said forward movement and juxtaposed in the direction of the movement wherein data obtained during the backward movement serves to enhance accuracy of the data obtained during the forward movement and juxtaposed in the direction of the movement, so that accuracy of interpolation performed in a direction of juxtaposition of imaginary cross-sectional slices of said subject on the basis of the data obtained in both the forward movement and the backward movement is increased two-fold from that of interpolation performed in a direction of juxtaposition of imaginary cross-sectional slices of said subject on the basis of the data obtained only during the forward movement.

4. The computerized tomography system according to claim 1 further comprising means for performing an adjustment so that the locus of said X-ray tube in forward movement of said subject bed and that of said X-ray tube in backward movement of said subject bed do not intersect with one another and data obtained during said backward movement comes in between two mutually adjacent data previously obtained during said forward movement and juxtaposed in the direction of the movement wherein data obtained during the backward movement serves to enhance accuracy of the data obtained during the forward movement and juxtaposed in the direction of the movement, so that accuracy of interpolation performed in a direction of uxtaposition of imaginary cross-sectional slices of said subject on the basis of the data obtained in both the forward movement and the backward movement is increased two-fold from that of interpolation performed in a direction of juxtaposition of imaginary cross-sectional 5. A computerized tomography system comprising an X-ray tube for generating X-rays, X-ray detectors opposed to said X-ray tube to detect X-rays transmitted through a subject, a frame which is continuously rotated while bearing said X-ray tube and said X-ray detectors, a bed which is moved while bearing said subject, means for moving said bed perpendicularly to a plane of revolution of said X-ray tube and synchronously with said revolution, and means for irradiating X-rays upon said subject from said X-ray tube during the movement of said bed to spirally scan said subject.

6. The computerized tomography system according to claim 5 further comprising means for moving said bed forward.

7. The computerized tomography system according to claim 5 further comprising means for moving said bed backward.

8. The computerized tomography system according to claim 5 further comprising means for moving said bed forward and backward.

9. A computerized tomography system including an X-ray tube for generating X-rays, X-ray detectors opposed to said X-ray tube to detect X-rays transmitted through a subject, a frame which is continuously rotated while bearing said X-ray tube and said X-ray detectors, and a bed which is moved while bearing said subject, said system comprising:

means for moving said bed perpendicularly to a plane of revolution of said X-ray tube and synchronously with said revolution;

means for irradiating said X-ray upon said subject from said X-ray tube during movement of said bed to spirally scan said subject;

buffer means for storing spiral data obtained by the means for irradiating said X-rays to spirally scan, said spiral data being stored in an address determined by a projection position number and a scanner rotation number;

an interpolation circuit for performing interpolation on said spiral data to obtain projection data; and an inverse projection calculating circuit for subjecting said projection data to inverse projection to recompose a tomogram.

10. The computerized tomography system according to claim 9 wherein said buffer means comprises at least one two-dimensional buffer for storing said spiral data.

11. The computerized tomography system according to claim 9 further comprising an interpolation section which comprises:

said buffer means;

said interpolation circuit connected to said buffer means; and a one-dimensional buffer connected to said interpolation circuit for receiving a result from said interpolation circuit.

12. The computerized tomography system according to claim 9 wherein said back projection calculating circuit comprises:

a first buffer;

a four-point interpolation circuit for performing four-neareby-point interpolation on contents of said first buffer;

a second buffer for receiving a result from said four-point interpolation circuit;

a counter;

a calculating circuit responsive to said counter for calculating a value of $L^2$ corresponding to coordinates x, y on a two-dimensional tomogram;

a divider for dividing contents of said second buffer by a value $L^2$; and an adder for adding a predetermined value stored in a third buffer to a value calculated by said divider, responsive to a command from a beam calculator.

13. A method of operating a computerized tomography system which includes an X-ray generator for producing X-rays, an X-ray detector array for detecting the X-rays transmitted through a subject, and a subject bed, said X-ray tube and said X-ray detectors being opposed to each other, X-ray beams being irradiated upon said subject in a sectorial manner at a large number of angles to scan said subject while said X-ray tube and said X-ray detactors are being revolved around said subject, said X-ray tube and said X-ray detectors remaining opposed to each other during the revolution, said method comprising the steps of:

rapidly and continuously revolving a frame bearing said X-ray tube;

moving said subject bed perpendicularly to a plane of revolution of said X-ray tube and moving said subject bed synchronously with the revolution of said X-ray tube;

scanning said subject along with the movement of said subject bed in a spiral with respect to a coordinate system positioned about an imaginary axis passing through said subject; and obtaining a reconstructed tomogram of an arbitrary cross-section within a range from a position corresponding to a beginning of the spiral scanning to a position corresponding to an end of the spiral scanning.

14. The method according to claim 13, further comprising the step of performing the spiral scanning along with forward and backward movement of said subject bed.

15. The method according to claim 13 further comprising the step of performing an adjustment so that the locus of said X-ray tube in forward movement of said subject bed and that of said X-ray tube in backward movement of said subject bed do not intersect with one another and data obtained during said backward movement comes in between two mutually adjacent data previously obtained during said forward movement and juxtaposed in the direction of the movement wherein data obtained during the backward movement serves to enhance accuracy of the data obtained during the forward movement and juxtaposed in the direction of the movement, so that accuracy of interpolation performed in a direction of juxtaposition of imaginary cross-sectional slices of said subject on the basis of the data obtained in both the forward movement and the backward movement is increased two-fold from that of interpolation performed in a direction of juxtaposition of imaginary cross-sectional slices of said subject on the basis of the data obtained only during the forward movement.

16. The method according to claim 13 further comprising the step of performing an adjustment so that the locus of said X-ray tube in forward movement of said subject bed and that of said X-ray tube in backward movement of said subject bed do not intersect with one another and data obtained during said backward movement comes in between two mutually adjacent data previously obtained during said forward movement and juxtaposed in the direction of the movement wherein data obtained during the backward movement serves to enhance accuracy of the data obtained during the forward movement and juxtaposed in the direction of the movement, so that accuracy of interpolation performed in a direction of juxtaposition of imaginary cross-sectional slices of said subject on the basis of the data obtained in both the forward movement and the backward movement is increased two-fold from that of interpolation performed in a direction of juxtaposition of imaginary cross-sectional slices of said subject on the basis of the data obtained only during the forward movement.

17. A method of operating a computerized tomography system including an X-ray tube for generating X-rays, X-ray detectors opposed to said X-ray tube to detect X-rays transmitted through a subject, a frame which is continuously rotated while bearing said X-ray tube and said X-ray detectors, a bed which is moved while bearing said subject, said method comprising the steps of moving said bed perpendicularly to a plane of revolution of said X-ray tube and synchronously with said revolution, and irradiating X-rays upon said subject from said X-ray tube during the movement of said bed to spirally scan said subject.

18. The method according to claim 17 further comprising the step of moving said bed forward.

19. The method according to claim 17 further comprising the step of moving said bed backward.

20. The method according to claim 17 further comprising the step of moving said bed forward and backward.

* * * * *